(12) United States Patent
Forber

(10) Patent No.: US 8,882,727 B2
(45) Date of Patent: Nov. 11, 2014

(54) NEEDLE HAVING A SAFETY DEVICE

(75) Inventor: Simon Forber, Liguge (FR)

(73) Assignee: B. Braun Medical SAS, Boulogne-Billancourt (FR)

( * ) Notice: Subject to any disclaimer, the term of this patent is extended or adjusted under 35 U.S.C. 154(b) by 0 days.

(21) Appl. No.: 13/513,790

(22) PCT Filed: Jun. 28, 2011

(86) PCT No.: PCT/EP2011/003162
§ 371 (c)(1),
(2), (4) Date: Feb. 27, 2013

(87) PCT Pub. No.: WO2012/000642
PCT Pub. Date: Jan. 5, 2012

(65) Prior Publication Data
US 2013/0172825 A1 Jul. 4, 2013

(30) Foreign Application Priority Data

Jun. 28, 2010 (FR) ..................................... 10 02701

(51) Int. Cl.
| | |
|---|---|
| *A61M 25/06* | (2006.01) |
| *A61M 39/02* | (2006.01) |
| *A61M 5/32* | (2006.01) |
| *A61M 5/158* | (2006.01) |

(52) U.S. Cl.
CPC ....... *A61M 25/0625* (2013.01); *A61M 39/0208* (2013.01); *A61M 2005/325* (2013.01); *A61M 2005/1583* (2013.01); *A61M 2005/1581* (2013.01); *A61M 5/3273* (2013.01)
USPC ....................... 604/263; 604/164.08; 604/192

(58) Field of Classification Search
CPC ..................... A61M 2005/1581; A61M 25/06
USPC ..................................... 604/164.08, 192, 263
See application file for complete search history.

(56) References Cited

U.S. PATENT DOCUMENTS

| | | | | |
|---|---|---|---|---|
| 6,629,959 | B2 * | 10/2003 | Kuracina et al. ............... | 604/192 |
| 7,569,044 | B2 * | 8/2009 | Triplett et al. ................. | 604/506 |
| 7,776,016 | B1 * | 8/2010 | Halseth et al. ................. | 604/162 |
| 8,491,527 | B2 * | 7/2013 | Triplett et al. ............. | 604/93.01 |
| 2003/0163098 | A1 * | 8/2003 | Fleury et al. .................. | 604/263 |
| 2005/0113761 | A1 * | 5/2005 | Faust et al. ..................... | 604/180 |
| 2007/0161953 | A1 * | 7/2007 | Chawki et al. ................. | 604/116 |
| 2009/0287159 | A1 * | 11/2009 | Triplett et al. ................. | 604/195 |

* cited by examiner

*Primary Examiner* — Nicholas Lucchesi
*Assistant Examiner* — Gerald Landry, II

(57) ABSTRACT

A needle has a distal end, a proximal end, and a stem extending there between, as well as a tip at the distal end. The needle is provided with a safety device being arranged so as to be capable of sliding over the stem and a second position at the distal end of the stem. The safety device also includes a recess having a proximal opening and a distal opening for the needle stem to pass there through, the tip of the needle being inside the recess when the safety device is in the second position. The device includes a closing device that closes the distal opening of the recess when the needle tip is inside the recess.

16 Claims, 3 Drawing Sheets

Fig. 2a
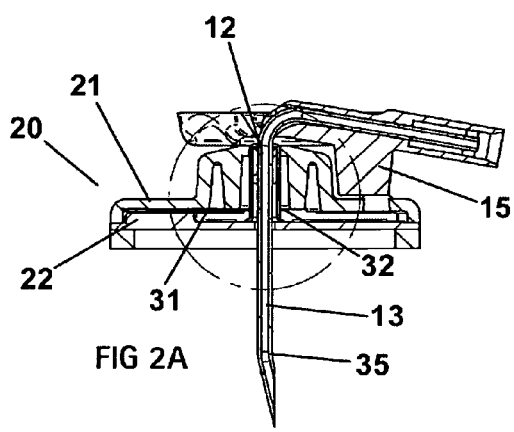
FIG 2A
Fig. 3a
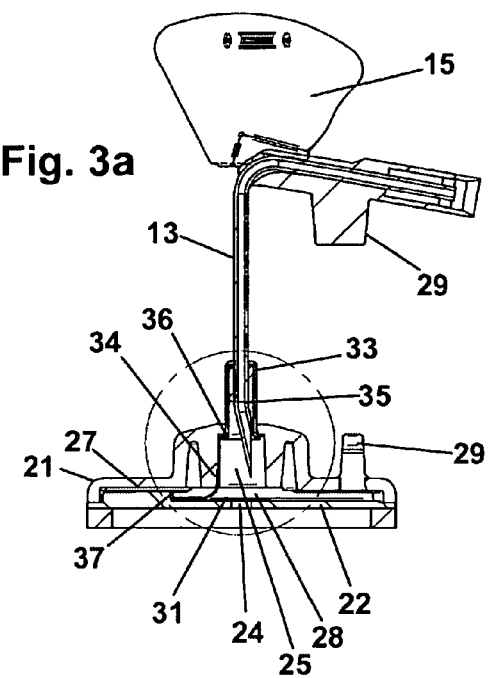
Fig. 2b
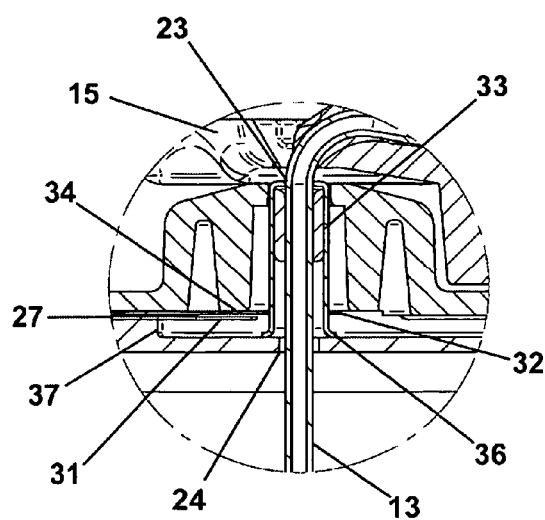
Fig. 3b
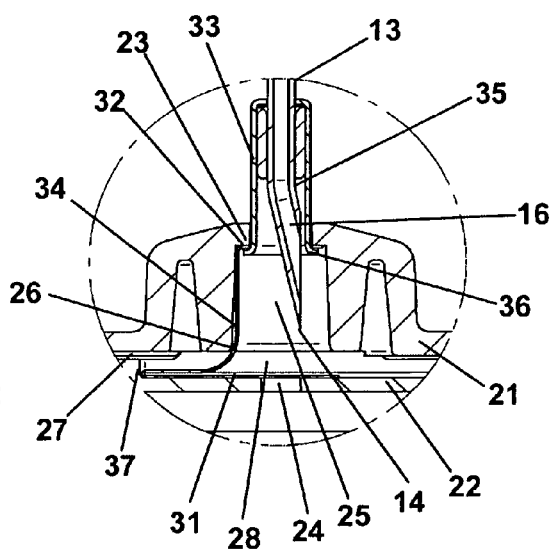

NEEDLE HAVING A SAFETY DEVICE

The present invention relates to a needle for the injection and the withdrawal of fluids with a safety device for protecting against injuries on the needle tip.

Needles of different types have been used in medicine for injecting fluids into a patient's body or for withdrawing them from him. All needles represent a considerable risk of injuries for the healthcare staff, especially after use when they are blood contaminated. To prevent any infection, it is consequently important to prevent injuries when removing the used needle.

Different safety devices for needles have been suggested in the past, which shall make the needle safe and especially the tip, which is dangerous once removed. The safety level and the comfort of use are however clearly insufficient.

Document FR 2 740 043 describes a protection device of a hypodermic needle comprising two flexible sheets at the proximal end of the needle which are first arranged perpendicular to the needle. After inserting the needle, the sheets are on the surface of the patient's skin. When removing the needle, a stop arranged above the sheets is held and offset downwards in the distal direction of the needle, which means that the sheets are brought away from their position perpendicular to the needle into a position parallel to the needle. The needle is thus surrounded laterally. The risk of injuries is reduced.

This solution still has major shortcomings. Removing the needle can only be performed by exerting a certain force since the flexible sheet must be deformed over a large area to surround the needle. Since the sheets bear against the patient's skin in the initial position, the sheets move over the skin when removing the needle, which may pinch the skin or exert force laterally on the needle. An additional mechanism must besides secure the safety device in the final position so that the needle tip cannot slide out of it.

Document U.S. Pat. No. 6,224,569 B1 discloses a safety device which lies in its starting position at the proximal end of the needle and can be moved in the form of a cylindrical sleeve along the needle in the distal direction. Two springs are arranged inside the device, which are held by a preload against the needle stem. If the device is moved along the needle stem in the distal direction, the distal end of the device is pushed beyond the needle tip and the tip penetrates inside the device. The stem of the needle releases the springs which fold up before the distal opening of the device. The needle tip is thus encased in the device.

A shortcoming of this device is however that it can only be displaced against the preloaded springs along the needle stem, which requires relatively great force. A stop is further provided so that the needle cannot be passed completely through the device. A stop on the needle stem can only be laid in the region which does not penetrate the patient's tissue. To that end, the needle needs to have a corresponding length and should be retractable sufficiently far into the safety device, which implies a relatively long safety device.

The object of the present invention is to suggest a safety device for a needle, especially a medical needle, which avoids the shortcomings described above and especially exhibits a flat assembly which makes the needle easily mobile and which surrounds its tip reliably upon activation of the device.

This is achieved according to the invention with a needle with a distal end, a proximal end and a stem extending therebetween as well as a tip at its distal end. The needle according to the invention is provided with a safety device for protecting against injuries on the tip of the needle, whereas the safety device is arranged so that it may slide over the stem between a first position in the proximal region of the stem and a second position at the distal extremity of the stem. The safety device has a closed housing with a proximal opening and a distal opening for letting the needle stem therethrough, whereas the needle tip is inside the housing when the safety device is in the second position. The safety device contains a closing device which closes the distal opening of the housing when the needle tip is inside the housing.

The needle according to the invention is characterised in that the closing device comprises at least one closure element which may slide from a first position away from the opening into a second position facing the opening. The closure element cooperates with an activation element which is arranged slidingly on the needle stem. A driver element which limits the stroke of the activation element on the needle stem in the distal direction is moreover arranged on the needle stem. The activation element moves, when sliding the safety device from its first to its second position, abutting the driver element, so that, when sliding the safety device further, the activation element moves the closure element from its first to its second position and thus closes the opening in the housing.

The needle according to the invention with the safety device enables safe use of the needle. In the first position of the safety device, the needle tip is released, and the needle is useable normally. Since it is still new and not used and generally packed sterilely, it does not present any particular risk for the healthcare medical staff. Even in the case of injury with the needle tip, there is still no risk of infection.

The needle is then inserted into a patient's tissue and used in the normal way. When removing the needle, the safety device is moved in the distal direction towards the needle tip. This first of all occurs without additional resistance caused by the safety device. Towards the end of the stroke, the closure element(s) are moved by abutting the activation element with the driver element form its (their) starting position(s) into a position facing the distal opening of the housing as soon as the needle tip is withdrawn inside the housing. The housing is thus closed entirely. Any injury of the healthcare staff with the tip of the contaminated needle is excluded.

In an embodiment of the invention, the needle can be Huber needle with a bent end. The transition between the straight section and the bent section then represents the driver element.

In a further embodiment, the driver element can be a portion of the stem of the needle having a modified cross-section. The cross-section can for example be locally oval instead of circular. The activation elements which slide over the circular portion of the stem abut the portion with oval cross-section and thus displace the closure elements.

The closure elements can preferably be connected to the activation element by arms, in particular by non-elastically deformable arms. It may be thus guaranteed that the closure elements cannot be pulled apart from the housing opening unintentionally any longer once the device is activated and the needle top cannot come out of the housing. The forces necessary to deform the arms are small so that activation of the safety device does not require any particular effort.

The activation element may comprise a sleeve which is arranged slidingly in the proximal opening of the housing. This permits a structure with particular little space requirements of the safety device.

The housing advantageously exhibits a chamber in the region of passage of the needle whose dimensions are suitable for receiving the section of the needle between driver element and needle tip. This chamber can be cylindrical.

The safety device of the needle according to the invention can especially have one or two closure elements.

Advantageously, the housing may have a stop which prevents the closure element from leaving the second position. This stop can notably be arranged on the bottom of the housing of the safety device laterally of the distal opening. The stop prevents the closure element, once it has reached its second position in front of the opening, from leaving this position.

For the needle to be manipulated easily, it may be provided with a base in the proximal region.

Since the safety device can slide over the needle stem without substantial friction resistance, in a preferred embodiment, a removable connection between the base and the safety device may be provided, notably a snap-on connection. Thus, early sliding of the safety device over the needle stem can be avoided. The connection is preferably easily removable so that it does not cause any problem during manipulation when removing the needle.

An embodiment of the invention is explained in more detail below using the appended figures:

FIGS. 2a and 2b illustrate the needle according to the invention according to FIG. 1 in cross section with the safety device in the first position, in partial magnification in FIG. 2b;

FIGS. 3a and 3b illustrate the needle according to the invention according to FIGS. 1 and 2 in cross section with the safety device in the second position, in partial magnification in FIG. 3b;

Figure 1:
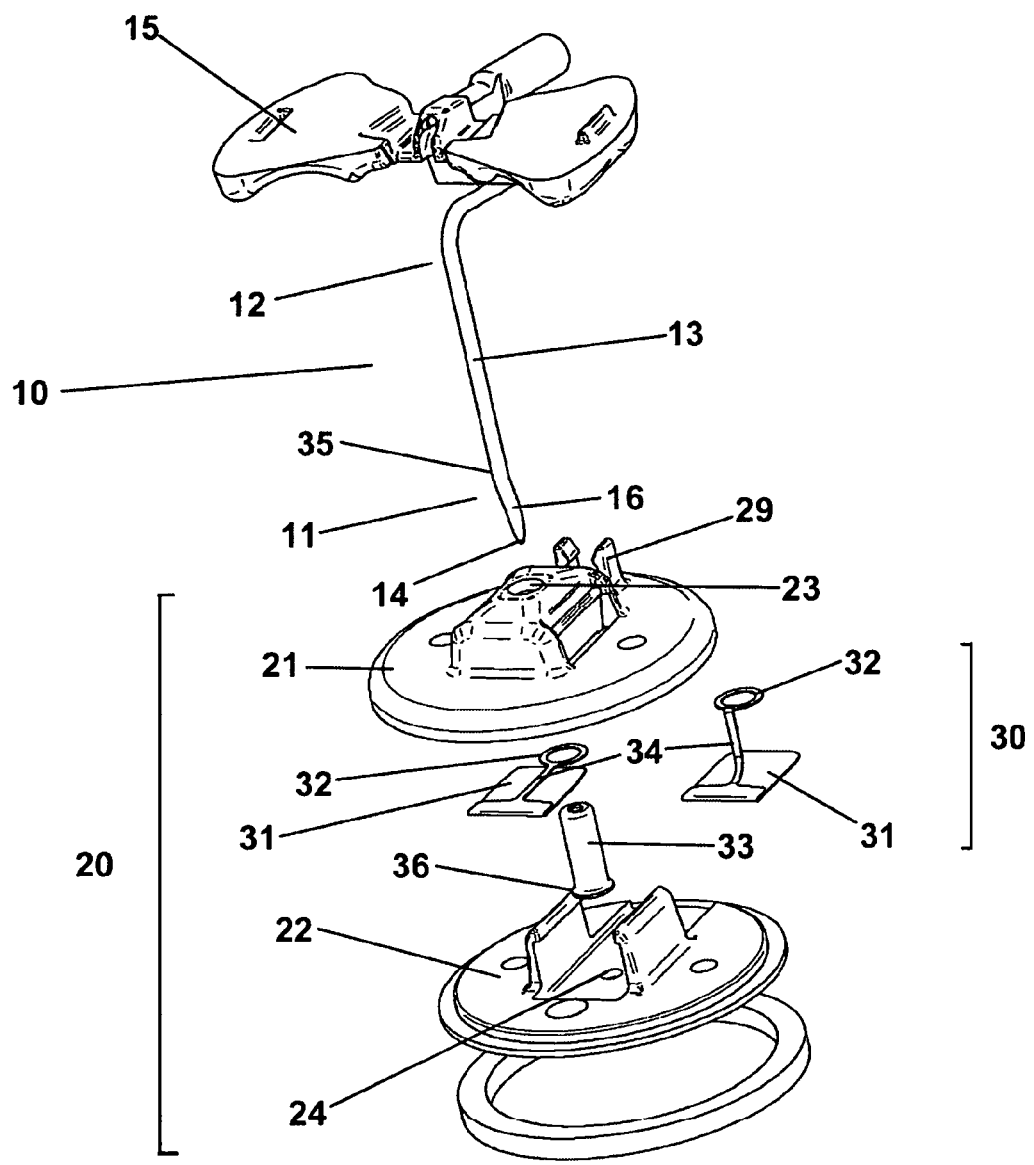
FIG. 1 illustrates a needle according to the invention with a safety device in an exploded view.

FIG. 1 illustrates a needle 10 according to the invention with a safety device 20 in an exploded view. The represented needle is a Huber needle in view of the use for implantable chambers, for the supply of drugs to a patient. The needle 10 has a bent needle portion 16 on the tip 14 for the puncture of the membrane of an implantable chamber.

The needle 10 has a distal end 11 with a bent tip 14 and a proximal end 12 which is provided with a base 15.

The needle 10 is moreover provided with a safety device 20 which is arranged slidingly on the stem 13 of the needle. The safety device 20 may slide thereon from a first position at the proximal end 12 of the needle stem 13 prior to using the needle to a second position at the distal end 11 of the needle 10 after use, in which the tip of the needle 24 is secured.

The safety device 20 consists of a housing containing a housing lid 21 and housing bottom 22. The housing lid 21 includes a proximal opening 23 which guides the housing by sliding over the needle stem 13. The bottom of the housing 22 has a distal opening 24 of the housing through which the needle may go through the housing.

A closure element 31 is arranged inside the housing 21, 22. The closure element is connected by means of a flexible arm 34 to a ring 32 which surrounds a sleeve 33 whose lower neck 36 has a diameter greater than the internal diameter of the ring 32. The sleeve 33 slides in assembled condition on the stem of the needle 13. The closure element 31, the arm 34 and the ring 32 are represented on the right on FIG. 1 in activated condition when the safety device 20 is after use in the second position at the distal end 11 of the needle 13. The representation on the left shows the closure element 31, the arm 34 and the ring 32 in the first position of the safety device 20 prior to use of the needle at the proximal end 12 of the stem 13 of the needle.

The safety device 20 is in the first position in the proximal region 12 of the stem 13 close to the base 15. The stem of the needle 13 extends, seen in the proximal towards distal direction, through the proximal opening 23 of the lid of the housing 21, through the sleeve 33 and through the distal opening of the housing 24 in the bottom of the housing 22 so that the needle tip 14 is freely accessible and the needle 10 can be used.

The needle 10 can then be inserted into a patient's tissue and used in the normal way. A ring 38 arranged on the bottom 22 of the housing can in this instance serve as a stop and then bears upon the patient's skin.

To remove the needle, the needle is seized with one hand at the base 15 and the safety device 20 is held in position by pressing with the other hand on the lid of the housing 21 when removing the needle 10.

The snap-on connection 29 which secures the safety device 20 in its first position is released and the needle stem 13 then slides through the safety device 20. No additional substantial friction force then acts in that particular instance between the needle stem 13 and the safety device 20 so that the needle can be removed easily from a patient's tissue.

The needle 10 may slide through the safety device 20 until the safety device 20 reaches the distal end 11 of the needle. As soon as the sleeve 33 meets the transition 35 towards the bent region 16 of the needle, the sleeve 33 cannot slide further and is carried along when moving the needle further. The sleeve 33 drives the ring 32 arranged on its lower neck 36, which ring is lifted by the sleeve 33 when moving the needle further. The connection arm 34 belonging to the closure element 31 is in that particular instance deformed non-elastically so that the closure element 31 is pulled inwardly and the distal opening of the housing 24 is closed. The lid of the housing 21 and the bottom of the housing 22 are designed to that effect so that the closure element 31 can be moved essentially in parallel to the bottom 22.

The closing device 30 then takes on the form illustrated on the right in FIG. 1.

The needle tip 14 is safely enclosed in the housing 21, 22 in the second position of the safety device. The closing device 30 cannot be brought back into the initial position due to the non-elastic deformation of the arm 34 so that an opening of the device by mistake and the needle tip coming out are impossible. The safety device 20 cannot slide from the needle 10 in the distal direction either since the bent needle section 16 cannot slide through the sleeve 33 which in turn cannot slide from the proximal opening 23 of the housing lid 21 due to its enlarged lower neck 36.

FIGS. 2a and 2b illustrate the needle with the safety device 20 of FIG. 1 in the first position before use, as a cross-sectional view. FIG. 2b is a partial enlargement of FIG. 2a.

The safety device 20 is in the first position in the proximal region 12 of the stem 13 close to the base 15. The needle traverses the housing 21, 22 of the safety device through the proximal and distal openings 23, 24. The base 15 and the safety device 20 are connected together by a snap-on connection to prevent unintentional sliding of the safety device 20 in the direction of the distal end 11 of the needle 10. The snap-on connection is however easily removable so as to guarantee troublefree withdrawal of the needle.

The closure element 31 is inside the housing 21, 22 close to the opening of the housing 24 through which the stem of the needle 13 goes. It can be seen that the closure element 31 is arranged in a slot 27 between the lid 21 and the bottom 22 of the housing a little higher than the level of the bottom 22.

In the enlargement of FIG. 2b, it can be clearly seen that the closure element 31 is connected by the arm 34 to a ring 32 which rests on the sleeve 33. The ring 32 and the sleeve 33 act as an activation element for the closure element 31 of the safety device when the safety device has moved into the second position.

The sleeve 33 is arranged slidingly in the proximal opening of the housing 23 and guides the stem of the needle 13.

For activation, the safety device is moved in the distal direction towards the needle tip 13 when removing the needle. The snap-on connection is first of all released between base 15 and safety device 29 so that the safety device 20 can slide over the needle stem 13. The needle stem is guided through the sleeve 33.

FIGS. 3a and 3b illustrate the needle with the safety device of FIGS. 1 and 2 in the second position after use, as a cross-sectional view. The needle tip is then secured in the device. FIG. 3b is again a partial enlargement of FIG. 3a.

If the needle is removed from the tissue after use, the base 15 is to that end seized with one hand while the other hand holds the housing 21, 22 of the safety device 20 in position. The snap-on connection 29 between base 15 and safety device 20 is released and the needle slides through the safety device, being guided by the sleeve 33. It slides up to its bent needle section 16 through the sleeve 33. The transition 35 towards the bent section 16 of the needle operates as a driver element. The needle cannot slide further through the sleeve 33. The sleeve is lifted on the needle in case of further sliding and then slides into the proximal opening 23 of the lid of the housing 21 upwards. The ring 32 is de facto also lifted on the lower neck 36 of the sleeve 33. The flexible arm 34 deforms non-elastically and pulls the closure element 31 inwardly in front of the distal opening 24 of the safety device. During displacement, the closure element 31 comes out of its first position in the slot 27, penetrates increasingly into the central compartment 28 of the housing and finally goes down the step 37 between the slot 27 and the central compartment 28, forced by the deformation of the flexible arm 34.

The tip of the needle 14 is then completely enclosed inside the housing 21, 22 and does not represent a danger any longer. The closure element 31 cannot be spaced apart from its position in front of the opening 24 due to the non-elastic deformation of the arm 34 since it abuts the step 37 between the central compartment 28 of the device and the slot 27 which acted as a housing for the closure element in its first position. Accordingly, the needle cannot come out of the housing unintentionally any longer.

It can be seen on FIGS. 2b and 3b that the flat shape of the housing 21, 22 with the cylindrical chamber 25 brings particular advantages. The housing 21, 22 has a flat design and offers on the upper side sufficient surface area to be held in position reliably with two fingers while the needle is removed. The closure element 31 is simultaneously held in a position parallel to the bottom 22. The cylindrical chamber 25 in which the sleeve 33 is in the first position contributes to deforming the arm 34 non-elastically, whereas the inward movement of the closure element 31 in the direction of the opening 24 is reinforced by the arm 34 bearing upon the ridge 26 of the cylindrical chamber 25. The cylindrical chamber 25 is sufficiently high for receiving the bent needle section 16 without increasing the design height of the safety device in the other regions of the housing.

Figure 4A:
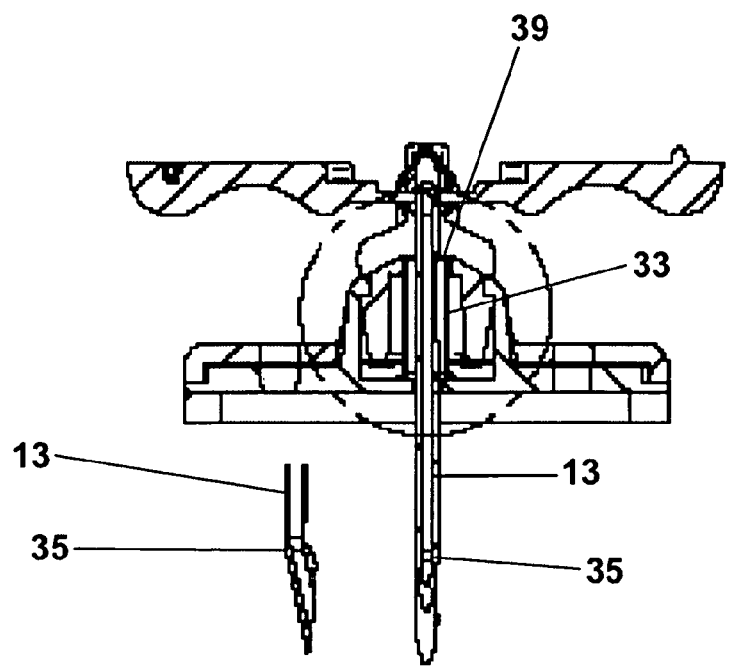
FIGS. 4a and 4b illustrate another embodiment of the invention, in the first position in FIG. 4a and in partial magnification in the second position in FIG. 4b.
Figure 4B:
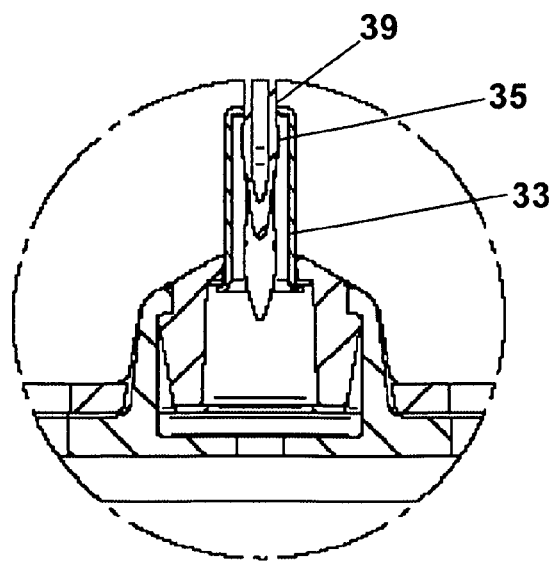

FIGS. 4a and 4b illustrate another embodiment of the invention, FIG. 4a shows an needle whose stem 13 has a circular cross-section and which exhibits a portion 35 with modified cross-section. The sleeve 33 includes a circular upper opening 39 adapted to the circular cross-section of the stem 13 of the needle. The portion with modified cross-section 35 is arranged on the stem 13 towards the end of the stroke of the safety device towards its second position. When the device slides over the stem 13 from the first to the second position, the opening 39 of the sleeve 33 abuts the portion with modified cross-section 35 as represented in partial enlargement in FIG. 4b. The portion with modified cross-section 35 represents the driver element. The closure elements that are not represented in this figure are then activated as described above for the embodiment of FIGS. 1 to 3.

The invention claimed is:

1. A needle,
having a distal end, a proximal end and a stem extending there between as well as a tip at its distal end,
provided with a safety device for protecting against injuries on the tip of the needle,
whereas the safety device is arranged so as to be able to slide over the stem between a first position in the proximal region of the stem and a second position at the distal end of the stem
and having a closed housing with a proximal opening and a distal opening for the needle stem to pass there through,
whereas the needle tip is situated inside the housing when the safety device is in the second position,
and the safety device comprises a closing device which closes the distal opening of the housing when the needle tip is situated inside the housing,
wherein,
the closing device comprises at least one closure element which may slide from a first position away from the opening into a second position facing the opening,
and cooperates with an activation element which is arranged slidingly on the needle stem,
and that a driver element which limits the stroke of the activation element on the needle stem in the distal direction is arranged on the needle stem,
and that the activation element abuts the driver element when the safety device slides from its first to its second position so that, when sliding the safety device further, the activation element moves the closure element from its first to its second position and thus closes the opening in the housing,
and wherein, a modification of the cross-section of the stem of the needle represents the driver element.

2. A needle,
having a distal end, a proximal end and a stem extending there between as well as a tip at its distal end,
provided with a safety device for protecting against injuries on the tip of the needle,
whereas the safety device is arranged so as to be able to slide over the stem between a first position in the proximal region of the stem and a second position at the distal end of the stem and having a closed housing with a proximal opening and a distal opening for the needle stem to pass there through,
whereas the needle tip is situated inside the housing when the safety device is in the second position,
and the safety device comprises a closing device which closes the distal opening of the housing when the needle tip is situated inside the housing,
wherein,
the closing device comprises at least one closure element which may slide from a first position away from the opening into a second position facing the opening,
and cooperates with an activation element which is arranged slidingly on the needle stem,
and that a driver element which limits the stroke of the activation element on the needle stem in the distal direction is arranged on the needle stem,
and that the activation element abuts the driver element when the safety device slides from its first to its second position so that, when sliding the safety device further, the activation element moves the closure element from its first to its second position and thus closes the opening in the housing, and wherein, the needle is a Huber needle and the transition between the straight section and the bent section represents the driver element.

3. The needle device according to claim 1, wherein, the closure elements are connected to the activation element by non-elastically deformable arms.

4. A needle according to claim 1, wherein, the activation element contains a sleeve which is arranged slidingly in the proximal opening of the housing.

5. A needle according to claim 1, wherein, the housing has an chamber in the passage area of the needle whose dimension is suitable for receiving the section of needle between the driver element (35) and the needle tip.

6. A needle according to claim 1, wherein, the safety device has one or two closure elements.

7. A needle according to claim 1, wherein, the housing has a stop which prevents the closure element from leaving the second position.

8. A needle according to claim 1, wherein, the needle has a base in the proximal region.

9. A needle according to claim 8, wherein, the base and the safety device are connected together removably in the first position especially through a snap-on connection section represents the driver element.

10. The needle according to claim 2, wherein, the closure elements are connected to the activation element by non-elastically deformable arms.

11. A needle according to claim 2, wherein, the activation element contains a sleeve which is arranged slidingly in the proximal opening of the housing.

12. A needle according to claim 2, wherein, the housing has an chamber in the passage area of the needle whose dimension is suitable for receiving the section of needle between the driver element (35) and the needle tip.

13. A needle according to claim 2, wherein, the safety device has one or two closure elements.

14. A needle according to claim 2, wherein, the housing has a stop which prevents the closure element from leaving the second position.

15. A needle according to claim 2, wherein, the needle has a base in the proximal region.

16. A needle according to claim 15, wherein, the base and the safety device are connected together removably in the first position especially through a snap-on connection.

* * * * *